(12) United States Patent
Cochrane et al.

(10) Patent No.: US 9,810,756 B2
(45) Date of Patent: Nov. 7, 2017

(54) ZERO- AND LOW-FIELD TRANSPORT DETECTION SYSTEM

(71) Applicants: Corey Cochrane, Burbank, CA (US); Patrick M. Lenahan, Boalsburg, PA (US)

(72) Inventors: Corey Cochrane, Burbank, CA (US); Patrick M. Lenahan, Boalsburg, PA (US)

(73) Assignee: The Penn State Research Foundation, University Park, PA (US)

( * ) Notice: Subject to any disclaimer, the term of this patent is extended or adjusted under 35 U.S.C. 154(b) by 834 days.

(21) Appl. No.: 14/050,615

(22) Filed: Oct. 10, 2013

(65) Prior Publication Data
US 2014/0247048 A1    Sep. 4, 2014

Related U.S. Application Data
(60) Provisional application No. 61/712,323, filed on Oct. 11, 2012.

(51) Int. Cl.
*G01V 3/00* (2006.01)
*G01R 33/385* (2006.01)
(Continued)

(52) U.S. Cl.
CPC ......... *G01R 33/385* (2013.01); *G01N 24/10* (2013.01); *G01R 33/24* (2013.01); *G01R 33/323* (2013.01)

(58) Field of Classification Search
CPC .. G01R 33/543; G01R 33/5611; G01R 33/36; G01R 33/4818; A61B 5/5055
(Continued)

(56) References Cited

U.S. PATENT DOCUMENTS

| 3,715,654 A | * | 2/1973 | Scarzello | ............... G01R 33/24 |
| | | | | 324/301 |
| 4,352,063 A | * | 9/1982 | Jones | ....................... A63C 5/06 |
| | | | | 324/168 |

(Continued)

OTHER PUBLICATIONS

"Robust Absolute Magnetometry with Organic Thin-Film Devices" by W. J. Baker, K. Ambal, D. P. Waters, R. Baarda, H. Morishita, K. van Schooten, D. R. McCamey, J. M. Lupton & C. Boehme, Nature Communications, 3:898 DOI: 10.1038/ncomms1895; published Jun. 12, 2012.

(Continued)

*Primary Examiner* — Walter L Lindsay, Jr.
*Assistant Examiner* — Frederick Wenderoth
(74) *Attorney, Agent, or Firm* — Buchanan Ingersoll & Rooney PC

(57) ABSTRACT

A sensing apparatus for detecting and determining the magnitude of a static magnetic field has a first set of coils capable of producing a sweeping, quasi static, magnetic field when driven by a direct current and a second set of coils, for magnetic field modulation, positioned between the first set of coils capable of producing a low-frequency (audio), oscillating magnetic field when driven by an oscillating current. The magnetic fields induce a current through the semiconductor device which sampled to identify changes as a function of sweeping, quasi static magnetic field. To create an apparatus for detecting and identifying atomic scale defects in fully processed devices, a radio frequency circuit with a resonant component is added which provides an oscillating electromagnetic field in a direction perpendicular to that of the static magnetic field produced by the first set of coils.

18 Claims, 9 Drawing Sheets

(51) Int. Cl.
*G01N 24/10* (2006.01)
*G01R 33/24* (2006.01)
*G01R 33/32* (2006.01)

(58) Field of Classification Search
USPC .......................................................... 324/322
See application file for complete search history.

(56) References Cited

U.S. PATENT DOCUMENTS

| | | | |
|---|---|---|---|
| 6,217,213 B1 | 4/2001 | Curry et al. | |
| 7,656,154 B2 | 2/2010 | Kawabata et al. | |
| 2003/0224103 A1* | 12/2003 | Akinaga | B82Y 10/00 427/127 |
| 2007/0120563 A1* | 5/2007 | Kawabata | G01R 33/0354 324/244.1 |
| 2009/0157146 A1* | 6/2009 | Linder | A61N 1/37217 607/60 |
| 2011/0175603 A1* | 7/2011 | Burtman | G01R 33/098 324/244 |
| 2012/0068705 A1 | 3/2012 | Utsumi et al. | |
| 2012/0176129 A1* | 7/2012 | Seeger | G01R 33/038 324/252 |
| 2013/0096652 A1* | 4/2013 | Ozawa | A61N 1/3787 607/61 |

OTHER PUBLICATIONS

International Search Report for PCT/US2013/064277 dated Sep. 4, 2014.
Written Opinion of the International Searching Authority for PCT/US2013/064277 dated Sep. 4, 2014.
Magnitorezistivny effekt. Mezhotraslevaya Internet-sistema poiska i sinteza fizicheskikh printsipov deistviya preobrazovatelei energii, 2008 [online] [retrieved on Jul. 1, 2014]. Retrieved from the Internet: <URL: http://www.heuristic.su/effects/catalog/est/byld/description/304/index.html>.

* cited by examiner

ZERO- AND LOW-FIELD TRANSPORT DETECTION SYSTEM

CROSS-REFERENCE TO RELATED APPLICATIONS

The present application claims priority to U.S. Provisional Patent Application No. 61/712,323, which was filed on Oct. 11, 2012. The entirety of U.S. Provisional Patent Application No. 61/712,323 is incorporated by reference herein.

GOVERNMENT LICENSE RIGHTS

This invention was made with government support under Contract No. W911NF-11-2-0032, awarded by the U.S. Army. The Government has certain rights in the invention.

FIELD OF INVENTION

The invention relates to sensing apparatus that detect magnetic fields and apparatus that use magnetic field detection to identify defects in devices, particularly semiconductor devices.

BACKGROUND OF THE INVENTION

Magnetic fields have measurable characteristics. Some materials and devices when placed is a magnetic field will cause changes in one or more of the measurable characteristics. Consequently, the art has developed a number of detection devices that rely upon changes in magnetic fields that occur when a material is placed in the magnetic field to reveal something about that material. Some industries, particularly semiconductor manufacturers, test products for defects by observing what happens when the semiconductor material is exposed to a magnetic field. Such testing is often done by using electron paramagnetic resonance (EPR) spectrometers. Conventional EPR spectrometers range in cost from several hundred thousand dollars to about one million dollars for state of the art systems. Considerably less sensitive and much less versatile systems can be purchased for as little as $25,000. Electrically detected magnetic resonance (EDMR) spectrometers can be built with modest modification to an EPR spectrometer and can offer multiple advantages over these systems in applications of defect detection in solid state electronics. They offer much higher sensitivity and a sensitivity limited exclusively to imperfections which play a role in the electronic behavior of the devices under study. But, the inexpensive EPR spectrometers would be very difficult to modify for EDMR. The space and power requirements for the more expensive EPR spectrometers are considerable, with typical systems utilizing power supplies of several kilowatts and chilled water heat exchangers and requiring footprints of ten or more square feet.

Although conventional EPR and EDMR spectrometers are quite powerful analytical tools for the evaluation of materials physics problems in solid-state electronic devices, the measurements are quite time consuming and generally require extensive sample preparation to allow for insertion of samples into specialized microwave resonant cavities. There is a need for a much less expensive and convenient scheme for EDMR evaluation of semiconducting device technology. Additionally, conventional EDMR measurements require very large magnetic fields (typically 0.35 Tesla or higher) which must be exceptionally stable and high frequency electromagnetic radiation (typically 9 GHz or higher). There is a need for a measurement device that can determine the magnitude of a static magnetic field and detect changes in a magnetic field without the need for the large magnetic field. A detection device that does not need a high field and microwave resonator would be considerably less expensive and permit far more straightforward measurements. Indeed, there is a need for a detection device that consumes less energy and has a smaller footprint than available EPR spectrometers and yet can be used for testing and in other applications where conventional EPR spectrometers are used.

SUMMARY OF THE INVENTION

We here disclose a technology based upon the same underlying physics that can be used as an absolute magnetic field sensor and a miniature low-field electrically detected magnetic resonance (EDMR) spectrometer. This spectrometer can be used with wafer probing stations to identify and quantify atomic scale defects present in a wide variety of semiconductor devices. The embodiments of our invention here disclosed provide a robust measurement of magnetic fields and a means for extremely sensitive measurement of spin dependent transport mechanisms within fully processed micro- and nano-electronic devices. We have discovered that certain spin dependent transport mechanisms including recombination (SDR) and tunneling (SDT) can be detected within micro- and nano-electronics in the absence of an oscillating magnetic field while sweeping a small external quasi-static magnetic field across zero field. This behavior is unexpected from the conventional theory of EDMR. Thus, there is quite significant potential for use of this new physics in many applications. In addition, the incorporation of a low frequency oscillating (radio frequency) electromagnetic field significantly increases the analytical power of the invention by making the detection of defects within fully processed devices directly quantitative.

More specifically we provide a sensing apparatus for detecting and determining the magnitude of a static magnetic field which has a first set of coils capable of producing a sweeping, quasi static, magnetic field when driven by a direct current and a second set of coils, for magnetic field modulation, positioned between the first set of coils capable of producing an oscillating magnetic field when driven by an oscillating current. A precision, bipolar current controller drives current through the first set of coils to create a linearly sweeping magnetic field. A signal generator drives an oscillating current through the second set of coils to create an oscillating magnetic field to modulate the field produced by the first set of coils. A voltage biased, semiconducting device with a known, low magnetic field magnetoresistance properties is positioned in between both sets of coils. An analog front end conditions the semiconducting device current before being sampled and an analog-to-digital converter samples the conditioned semiconducting device current. A signal processing unit is capable of demodulating the conditioned sampled semiconducting device current and records changes in this signal as a function of sweeping, quasi static magnetic field. We prefer that the coils in each set of coils are Helmholtz coils. The signal processing unit may be a personal computer, microprocessor or microcontroller. The signal processing unit can self-calibrate itself with the already known parameters of the measured magnetoresistance response and can calculate the static magnetic field by measuring the shift in the measured magnetoresistance response of the semiconducting device away from zero magnetic field.

We also provide a similar apparatus for detecting and identifying atomic scale defects in fully processed devices which has a first set of coils capable of producing a sweeping, quasi static, magnetic field when driven by a direct current and a second set of coils, for magnetic field modulation, positioned between the first set of coils and capable of producing an oscillating magnetic field when driven by an oscillating current. The second set of coils is spaced far enough apart to enclose a voltage biased, semiconducting device with an unknown resonant and zero-field magnetoresistance response. A precision, bipolar current controller drives current through the first set of coils to create a linearly sweeping magnetic field and a signal generator drives an oscillating current through the second set of coils to create an oscillating magnetic field to modulate the field produced by the first set of coils. A radio frequency circuit with a resonant component provides an oscillating electromagnetic field in a direction perpendicular to that of the static magnetic field produced by the first set of coils. An analog front end conditions the semiconducting device current before being sampled. An analog-to-digital converter samples the conditioned semiconducting device current and a signal processing unit capable of demodulating the conditioned sampled semiconducting device current and records changes in this signal as a function of sweeping, quasi static magnetic field.

The technology described herein can also provide a much more inexpensive, robust, and lightweight alternative to costly (>$10,000) low-field based magnetic resonance magnetometers. A drawback of our alternative may be lower precision, at least in comparison with the highest precision systems. However, the devices described herein also provide absolute highly repeatable measurements due to the inherent self-calibrating capabilities of the device. They could also, at least in principle, offer higher sensitivity over currently available magnetic resonance based magnetometers.

Other objects and advantages of the present invention will become apparent from certain present preferred embodiments thereof shown in the drawings.

BRIEF DESCRIPTION OF THE DRAWINGS

FIG. 4(a) is a simulation of the recombination current for a 4H SiC diode at room temperature.

FIG. 4(b) is an illustration of the peak-to-peak amplitude of the zero-field signal as a function of applied bias plotted against the simulated recombination current displayed in FIG. 4(a) and the DC diode current in which the close similarity of the plots demonstrates that this phenomenon is a recombination process.

FIG. 4(c) is a graph showing the percent change in the zero-field SDR current acquired by dividing the peak-to-peak amplitude by the dc current as a function of bias voltage.

FIG. 4(d) is an integrated spectra acquired for the data plotted in FIGS. 4(b) and 4(c). Note that as the bias is increased beyond the built-in voltage ($V_a \geq 2.65$ V), the SDR signal begins to decrease. Note also that beyond this voltage, a double peak appears to be forming. The four traces on the inset of this figure illustrate the transition of the single peak into two.

DESCRIPTION OF PREFERRED EMBODIMENTS

Figure 1:
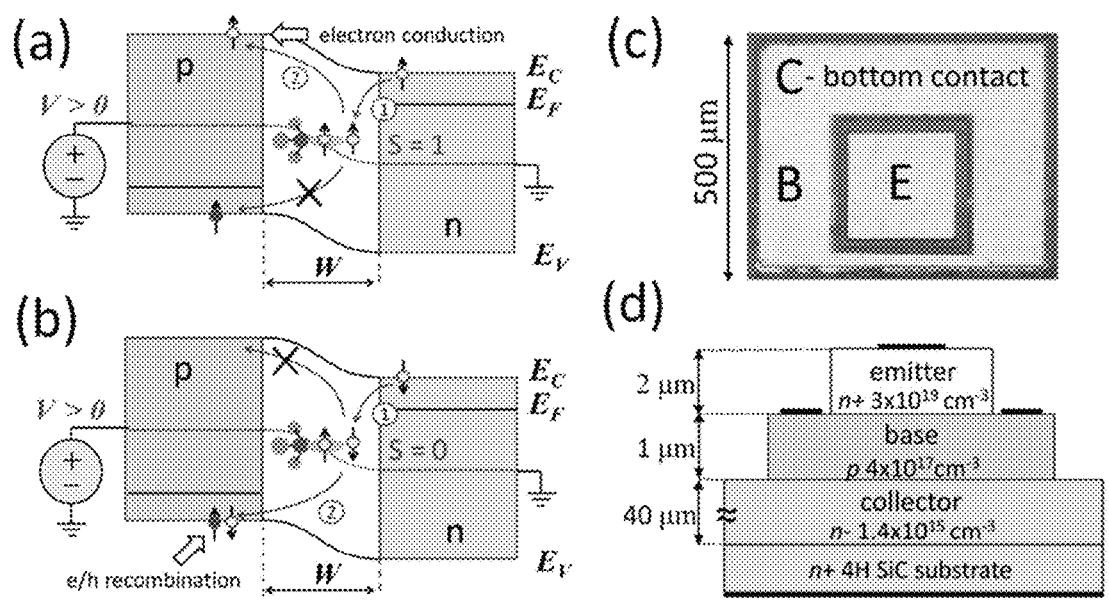
FIG. 1(a) is a diagram illustrating a semiconductor material having defects.
FIG. 1(b) is a diagram similar to FIG. 1(a) illustrating how a conduction electron and a defect electron couple to form a singlet pair.
FIGS. 1(c) and 1(d) are a top view and a cross-sectional view of a semiconductor device used in our study.

Electrically detected magnetic resonance (EDMR) is an electron paramagnetic resonance (EPR) technique that allows the study of atomic scale defect centers and electronic transport mechanisms in micro- and nano-electronics such as recombination, scattering, hopping, and tunneling. EDMR's sensitivity is many orders of magnitude greater than EPR; yet it retains the analytical power of the conventional technique. In EDMR via spin dependent recombination (SDR), a conduction electron or valence band hole can be trapped by a paramagnetic defect in which they are in close enough proximity to form an intermediate spin pair state. The basis states of these formed pairs will consist of either the symmetric triplet states $T_+=\uparrow\uparrow$, $T_0=(\uparrow\downarrow+\downarrow\uparrow)/\sqrt{2}$, $T_-=\downarrow\downarrow$, each having spin angular momentum S=1 or the anti-symmetric singlet state, $S_0=(\uparrow\downarrow-\downarrow\uparrow)/\sqrt{2}$ which has a spin angular momentum S=0. (The arrows in this case indicate the orientation of the spins.) If spin orbit coupling is negligible, the total angular momentum will be defined solely by the spin of the pair. Because recombination involves the annihilation of an electron and a hole, the process involves zero change in angular momentum. In order to conserve angular momentum, recombination is only possible after singlet pair formation. (If the system experiences significant spin-orbit coupling, the possibility of a triplet pair recombination event becomes possible.) FIGS. 1(a) and 1(b) illustrate this process in a forward biased pn junction. The magnetic resonance condition of SDR may be understood in terms of a spin Hamiltonian. Neglecting the small nuclear/field interaction, the spin Hamiltonian for an individual electron may be expressed by $$\hat{H} = \mu_\beta B^T \cdot g \cdot \hat{S} + \sum_i \hat{S}^T \cdot A_i \cdot \hat{I}_i \quad (1)$$

where $\mu_B$ is the Bohr magneton, B is the magnetic field vector, g is the electron g dyadic, and $\hat{S}$ is the electron spin operator. The index i refers to the hyperfine interaction of the ith nucleus with the electronic moment, $\hat{I}_i$ represents the nuclear spin operators for the different nuclei, and $A_i$ are the hyperfine parameters for those nuclei. In the absence of a nearby nuclear moment, resonance is obtained when the energy E of the applied $B_1$ oscillating electromagnetic field equals the Zeeman energy of either of the electrons in the spin pair, $h\upsilon=g\mu_B B_r$. Here, h is Planck's constant, $\upsilon$ is the frequency of the oscillating magnetic field, and $B_r$ is the field at resonance. If magnetic nuclei are present, a more complex spectrum results, essentially one resonant condition for each possible combination of local fields produced by the magnetic nuclei. At resonance, the oscillating $B_1$ magnetic field flips the electron's spin, thus randomizing the pairing's relative spin orientation. This process allows triplet states to transition into singlet states, thereby increasing the number of electrons that can recombine with holes. This increase due to resonance is typically measured as a change in current when sweeping a quasi-static magnetic field. However, in the absence of an oscillating $B_1$ magnetic field, this response is not anticipated.

Certain measurements were made on the base/collector junction diode of a 4H SiC n-p-n bipolar junction transistor (BJT) with an area of 500×500 μm². These devices, illustrated in FIGS. 1(c) and 1(d), consist of a 40 μm thick n-type collector doped with nitrogen at $1.4\times10^{15}$ cm$^{-3}$, a 1 μm thick p-type base doped with aluminum at $4\times10^{17}$ cm$^{-3}$, and a 2 μm thick n-type epitaxial emitter doped with nitrogen at $3\times10^{19}$ cm$^{-3}$. The EDMR measurements were made at room temperature on a custom built spectrometer composed of a Gaussmeter, a quintuple Helmholtz electromagnet to produce the static $B_0$ magnetic field, and a power supply controlled by a digital PI controller. The power supply used linearly passes through zero with no polarity switching. A current preamplifier conditioned and amplified the device currents before digitizing with a 16-bit analog to digital converter. For some measurements, the spectrometer utilized an RF signal generator which drives a solenoid in an RF resonant circuit to produce a $B_1$ oscillating magnetic field at 200 MHz. We utilized magnetic field modulation at 1 kHz via an additional set of Helmholtz coils. The modulated spin dependent current was demodulated using a custom designed multiband, virtual lock-in amplifier. Even though these effects can be observed in a single scan, adaptive signal averaging methods were utilized to more quickly resolve the hyperfine interactions.

In this study, we observed a magnetic field induced, change in current in a forward biased 4H silicon carbide (SiC) diode in the absence of electromagnetic radiation at zero magnetic field. We refer to this phenomenon as zero-field SDR (ZFSDR). We have observed this effect in multiple SiC based devices and observe a similar phenomenon with spin dependent tunneling (SDT) in 50 Å amorphous SiC:H capacitors. We show that by utilizing low frequency magnetic field modulation, one can clearly resolve electron-nuclear hyperfine interactions at low magnetic fields. We also show that the zero-field response versus voltage is in excellent agreement with the recombination current expected in the space charge region of a pn junction, clearly demonstrating that SDR is the underlying physical mechanism of this response.

A. Zero-Field Response

Figure 2:
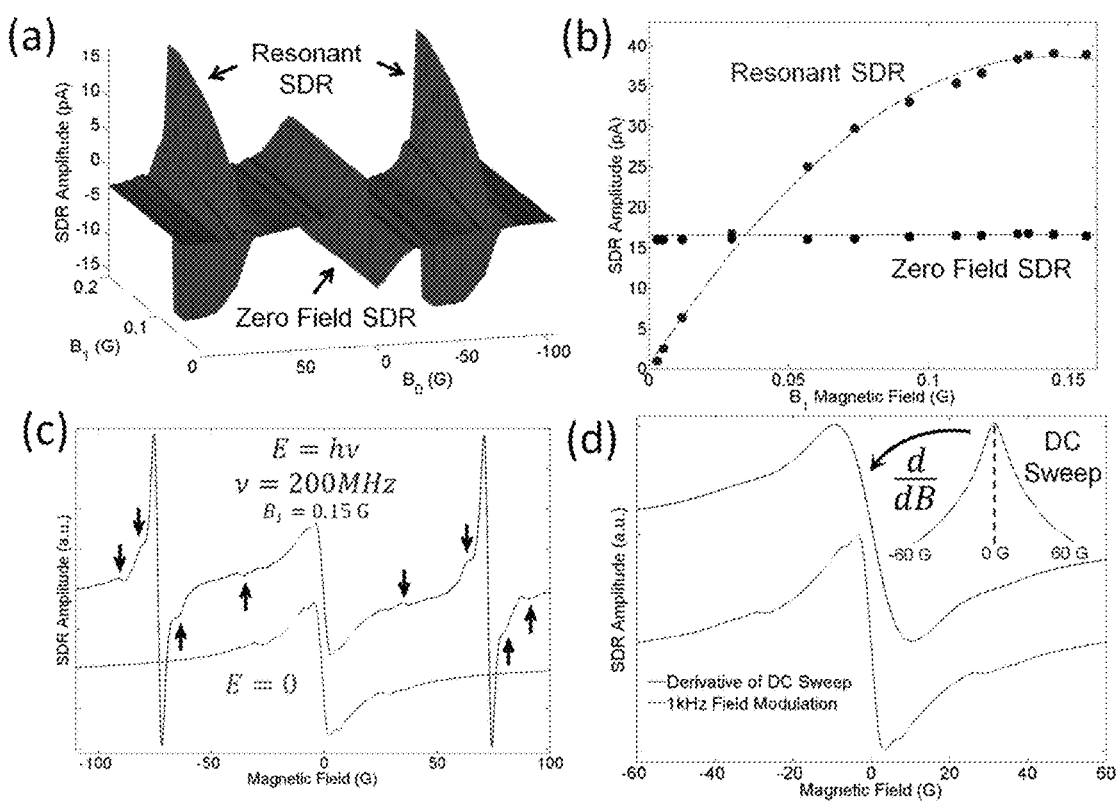
FIG. 2(a) is a 3D mesh of representative EDMR scans on a SiC diode for a series of $B_1$ amplitudes.
FIG. 2(b) is a graph of a the amplitude of the zero-field and low-field resonant signals as a function of $B_1$.
FIG. 2(c) is a comparison of low-field scans acquired with (top line) and without (bottom line) RF radiation applied. The arrows in the resonant trace indicate the Breit-Rabi shift of the normally (high-field) isotropic hyperfine peaks at low-fields.
FIG. 2(d) is a comparison of the derivative of a spectrum acquired without any modulation (top line) and a spectrum obtained from a 1 kHz, 2 Gauss modulation (bottom line).

A mesh plot of representative low-field EDMR responses is illustrated in FIG. 2(a) while subjecting the device to an oscillating RF magnetic field at 200 MHz at various $B_1$ amplitudes. Three distinct signals are apparent. The line centered at zero Gauss was not expected; however, the signals centered at ±71G are consistent with the conventional EPR resonance conditions. The amplitudes of the zero-field and resonant signals are plotted in FIG. 2(b) as a function of $B_1$. The EDMR amplitudes increase monotonically with increasing $B_1$. Note that the increase in the $B_1$ field saturates the resonant SDR response but doesn't affect the amplitude of the zero-field response. The fully saturated resonant signal is about 2.35 times larger than that of the zero-field signal. FIG. 2(c) compares the spectra obtained with and without the $B_1$ oscillating magnetic field. Note that because of the low-field condition, the normally (high-field) isotropic hyperfine peaks, indicated by the arrows in the figure are shifted towards zero Gauss. This is an observation consistent with the Breit-Rabi correction discussed in G. Breit, I. Rabi, *Phys. Rev.*, 38, 2082 (1931).

As expected, the resonant signals are no longer present in the trace without application of the RF radiation; however, the zero-field signal remains. At exactly zero-field, the axis of quantization is defined by the field the electron experiences from its local magnetic environment; while at relatively high magnetic fields (3 kG), it is defined primarily by the externally applied field. At low fields (<100 G) however, the field the electron experiences is the vector sum of the electron's local magnetic surroundings and externally applied magnetic field. As a result, the distribution of the spin pair's relative orientation will gradually be modified as zero-field is approached. Modifying the distribution of the spin pair's orientation essentially modifies the singlet-to-triplet ratio and hence, the recombination current. The zero-field spin pair distribution is not necessarily random as is the case for resonance. If they were, one would expect the amplitude of the saturated resonant and zero-field SDR responses to be equal which are clearly not as illustrated in FIGS. 2(a) and 2(b). This idea of a gradually changing spin pair orientation distribution also explains why line broadening is observed in the ZFSDR response. This SDR detection mechanism also applies to the defect sites which experience a hyperfine induced magnetic field due to neighboring magnetic Si, C, and N nuclei. When a defect site is coupled to one or more magnetic nuclei, it experiences a hyperfine field that can be "cancelled" by the slowly varying $B_0$ field. As a result, a response due to this interaction is observed away from 0 Gauss, at a field essentially corresponding to the magnitude of the hyperfine field. FIG. 2(d) compares the zero-field response detected with and without magnetic field modulation. As illustrated, utilizing lock-in amplification for demodulation greatly enhances the resolution of the spectrum. This technique essentially makes SDR sensitive to a single frequency, phase, and field direction. The peak-to-peak width of the spectrum without magnetic field modulation is approximately 20 Gauss and reveals only slight hints of hyperfine side peaks when the derivative is taken. The spectrum acquired with magnetic field modulation of 2 Gauss at 1 KHz has a central peak-to-peak width of only about 6 Gauss and quite significantly more visible hyperfine side peaks.

B. Hyperfine Interactions

Figure 3:
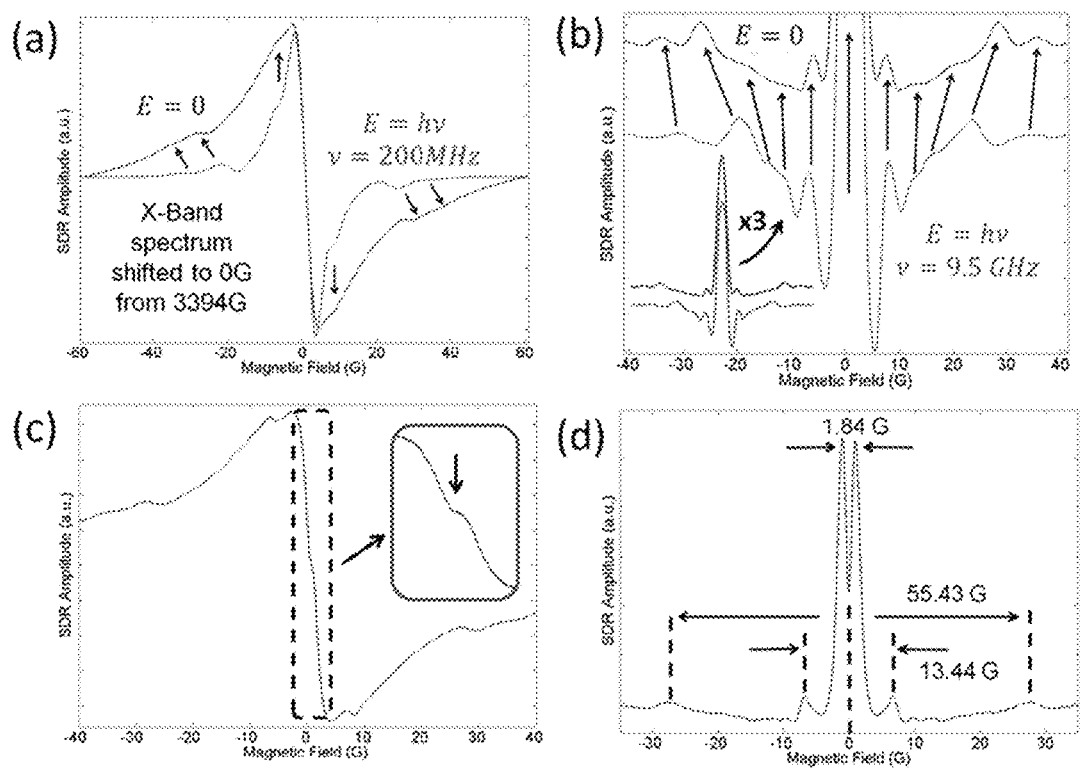
FIG. 3(a) is a first derivative of spectra observed at zero field (E=0) and at X band (E=hv, v=200 MHz) taken at 9.5 GHz, 3394 Gauss.
FIG. 3(b) is a second derivative of the spectra illustrated in FIG. 3(a) in which each peak observed at X band is also seen in the zero field spectrum.
FIG. 3(c) is a zero-field spectra.
FIG. 3(d) is a derivative of spectrum acquired with low modulation amplitude (~0.25 Gauss) in which the deviation in slope at precisely zero Gauss illustrated by inset FIG. 3(c) which shows up as a double peak in FIG. 4(d).

To further investigate the hyperfine interactions of the zero-field response, we compared the results to that of the high-field resonant response. FIG. 3(a) compares the zero-field and at X-band (9.5 GHz, 3394 G) spectra and FIG. 3(b) compares their derivatives. (The derivatives are used to enhance the observation of the hyperfine interactions.) For each side peak present in the X-band spectrum, a similar corresponding peak is present in the ZFSDR spectrum. Although a convincing identification of the defect (or defects) responsible for the EDMR spectrum is not yet determined, a plausible identification would be a defect aggregate. Although the hyperfine interaction peaks in the X-band and ZFSDR traces are not in precisely the same location with respect to the center line, the overall patterns are closely correlated. An exact correspondence should not be expected for several reasons. Among them, at extremely low external fields, the nuclear magnetic moment quantization axis is likely different than what it would be at high field because the local magnetic field experienced by the nuclei is not dominated by the applied field but by the field due to the nearby unpaired electron. As a result, the hyperfine interactions are somewhat modified. FIGS. 3(c) and 3(d) illustrate the spectrum and its derivative obtained when reducing the modulation amplitude to 0.25 Gauss, respectively. Notice the inflection point precisely at zero Gauss which is significantly more obvious when the derivative is taken as illustrated by the double peak in FIG. 3(d).

The ideas expressed with regard to hyperfine interactions and zero-field spin dependent phenomena are similar to those expressed by others to explain magnetic field effects on tunneling in double quantum dots and magneto-resistive effects in organic semiconductors. In both of these cases however, the hyperfine interactions invoked involved a multitude of unequal, essentially random, distributions of interactions which failed to yield a simple distinguishable pattern of hyperfine spectra or an unambiguous interpretation of the details of the spin dependent response. Because our measurements utilize single crystal devices, the random distribution of hyperfine fields is replaced by one which is not random and therefore allows direct correlation with a more conventionally observed pattern of hyperfine interactions.

C. Demonstration of Recombination

Because our zero-field response takes place in a well understood pn junction, we can directly demonstrate that its root cause is spin dependent recombination. Assuming a uniform distribution of trapping centers, to first order, the recombination current within the space charge region of a p-n junction can be described by $$J_r = \frac{q n_i W}{2} \cdot v_{th} N_t \sigma \cdot \exp\left[\frac{qV_a}{2kT}\right] \quad (2)$$

where $v_{th}$ is the thermal velocity, $N_t$ is the density of recombination defects, $\sigma$ is the capture cross section of the defect, $n_i$ is the intrinsic carrier concentration for 4H SiC at room temperature, $V_a$ is the junction bias, and W is the width of the depletion region. If the forward bias is close to the total built-in voltage, the depletion width is given by $$W = \left[\frac{2\varepsilon(N_a + N_d)(V_{bi} - V_a)}{qN_a N_d}\right]^{1/2} \quad (3)$$

where $\in$ is the permittivity of the semiconductor, $N_a$ is the density of ionized impurity acceptor atoms, $N_d$ is the density of ionized impurity donor atoms, and $V_{bi}$ is the built-in voltage which is defined as $$V_{bi} = \frac{kT}{q} \cdot \ln\left(\frac{N_a N_d}{n_i^2}\right) \quad (4)$$

Figure 4:
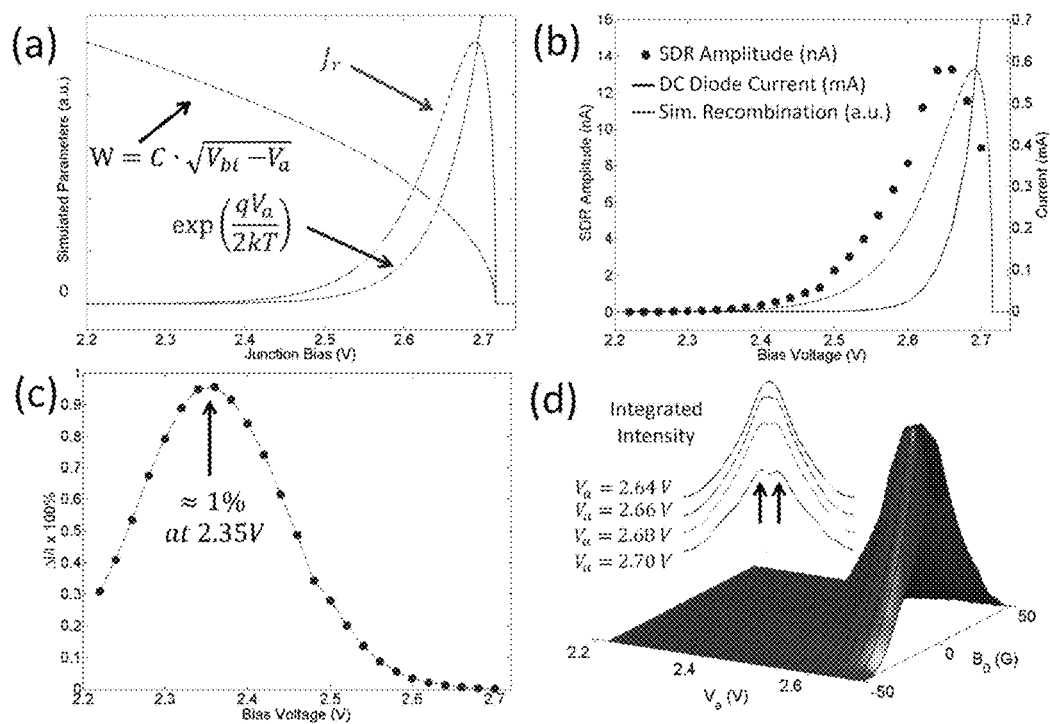
FIGS. 4(a) through 4(d) illustrate the behavior of the zero-field response as a function of applied bias.

Although some of the parameters in the previous equations are not precisely known, the relative amplitude of the recombination current versus applied bias can be calculated with moderate accuracy using the following, $$J_r = C \cdot \sqrt{V_{bi} - V_a} \cdot \exp\left[\frac{qV_a}{2kT}\right], \text{ for } V_a < V_{bi}, \quad (5)$$

where the built in voltage $V_{bi}$ is accurately known and C is a device dependent constant immaterial in our case. Once the applied junction voltage exceeds the built in voltage, the depletion region ceases to exist. This response is plotted in FIG. 4(a). We measured the peak-to-peak amplitude of the zero-field response as a function of applied bias and plotted it against the recombination current calculation illustrated in FIG. 4(b). The correspondence is extremely close indicating that the zero-field phenomenon is certainly due to SDR in the diode's space charge region. Plotted in FIG. 4(c) is the percent change in SDR current versus applied bias which is simply calculated by dividing the zero-field peak-to-peak amplitude by DC diode current (ΔI/I). Note that this response peaks at 2.35 volts with a relatively large change of almost 1%. The maximum response is almost 1% at a bias of 2.35.V. This is an exceedingly large effect at such small magnetic fields, but it is consistent with SDR phenomena involving triplet/singlet transitions as proposed by Kaplan et al in D. Kaplan, I. Solomon, N. F. Mott, *J. Phys. Lett. (Paris)*, vol. 39, no. 4, pp. L51-L54, (1978).

FIG. 4(d) illustrates the integrated data that was acquired used to plot the data points in FIGS. 4(b) and 4(c). Note that at significantly high junction biases ($V_a \geq 2.65$ V), the SDR signal begins to reduce in amplitude. Also, the inflection discussed earlier and illustrated in FIGS. 3(c) and 3(d) becomes more prominent and can be observed in the integrated intensity spectra. At this time, we are unsure why this is observed and cannot speculate any further on its nature.

The 1% change in recombination current at zero field is so large that it has many potential applications. One particular application that stands out among others is a sensor that provides absolute magnetometry (with directional polarity) which utilizes lock-in based detection when used with a precision current controlled magnetic field sweep. It has already been argued that somewhat similar phenomenon involved in low-field EDMR in organic devices may be useful for absolute magnetometry. However, utilizing the ZFSDR phenomenon in SiC devices has many advantages over organic devices. Unlike organic devices, SiC devices are inherently quite robust, and capable of very long term operation in challenging environments including high temperatures. Perhaps more importantly, SiC devices utilize a single crystal which allows for the detection of multiple sets of quite stable hyperfine interactions which can be used for magnetic field calibration without the requirement of RF components. For example, the 3 pairs of symmetrical peaks illustrated in FIG. 3(d) would serve as stable magnetic field markers as they would not move as a result of changes in biasing condition and or temperatures. Essentially, the magnetometer would be self-calibrating. It may also be useful to note that it has been suggested that SiC also has great potential in quantum computation for several reasons: its large bandgap allows for multiple defect-induced states; SiC defects are known to have long spin relaxation times; and the defects observed in this study involve sites with multiple nuclear spins (almost certainly Si and N) that can act as a universal quantum gate. And finally, because this ZFSDR phenomenon can be observed in multiple solid state electronic components including MOSFETs, BJTs, diodes, and capacitors, it would be useful for semiconducting manufacturing companies to incorporate simple automated low-field/zero-field EDMR spectrometers into wafer fabrication/probing equipment to study the defects in solid-state electronics during fabrication. Because only very low fields are required, low-field EDMR and ZFSDR can be performed easily and inexpensively.

Magnetic Field Sensing

Figure 5:
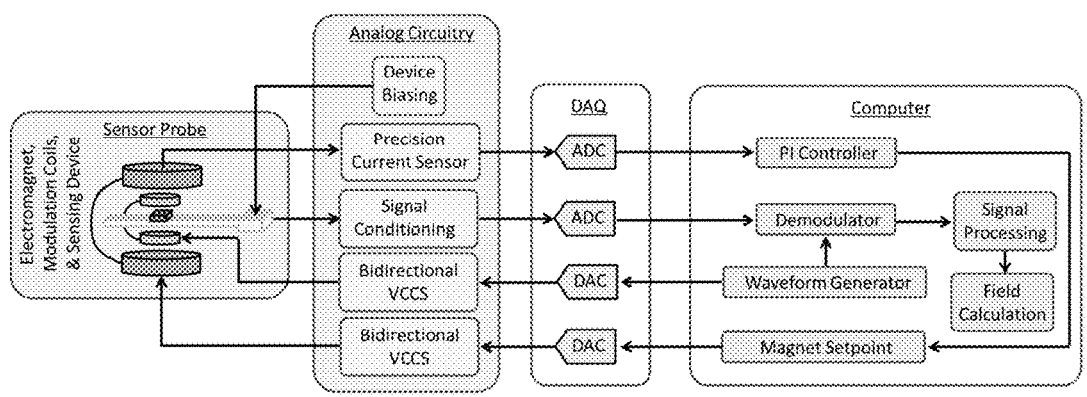
FIG. 5 is a diagram of present preferred embodiment of a magnetic field sensor in accordance with the present invention.

The zero-field SDR and SDT responses that are observed in silicon carbide (SiC) based microelectronic devices (bipolar junction transistors (BJTs), metal-oxide-semiconducting field-effect transistors (MOSFETs), and capacitors) provide the ideal physics for absolute magnetometry at very low cost with a highly robust device. Other inorganic material systems other than SiC could also quite likely provide comparable physics. Some of these material systems include Si, Ge, CdTe, and CdS as other likely candidates. The underlying idea behind the functionality of the sensor is the presence of the zero-field SDR (or SDT) signal. This signal is strongest at zero-field and can extend, with a very repeatable structure, up from to zero to small magnetic fields. In the specific device that we used, the repeatable structure was observed as side peaks that arise from electron nuclear hyperfine interactions at magnetic fields slightly larger than zero. These extremely stable peaks allow us to calibrate the sensor and precisely measure the external magnetic field. As illustrated in FIG. 5, the sensor is comprised of a SiC based sensing device, a set of Helmholtz coils to provide a sweeping magnetic field (electromagnet), an additional set of Helmholtz coils to provide magnetic field modulation, a device biasing source, and a current-to-voltage preamplifier with analog signal conditioning capabilities. In addition, a precision current controller is implemented for the electromagnet so that the static magnetic field produced can be easily determined. By precisely controlling the current, the magnetic field produced by the electromagnet is indirectly, but precisely, known. Magnetic field control is not utilized because the controller would compensate for the magnetic field one is attempting to detect. The remainder of the technology is implemented in software. More specifically, a digital PI controller, lock-in amplification, digital signal processing, and field prediction are implemented by a computer that is connected to the analog circuitry through a serial bus. A digital signal processor/microcontroller could also be used instead of a computer to perform the required ADCs, DACs, control, and processing to make the unit quite portable.

Figure 6:
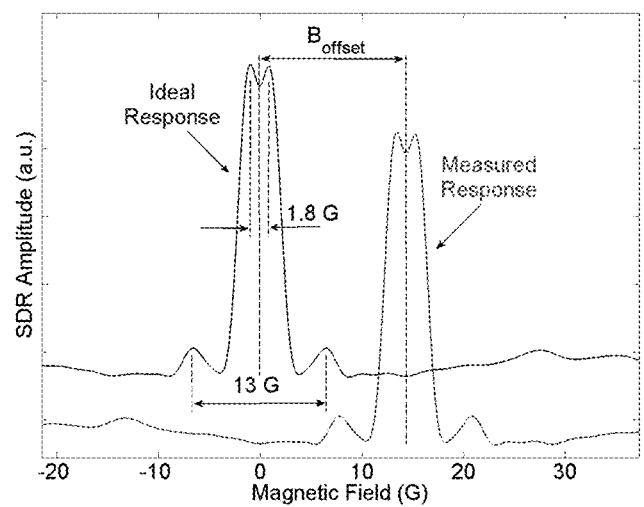
FIG. 6 is a graph showing of the response of the sensor of FIG. 5 in the presence and absence of a magnetic field.

The sensor shown in FIG. 5 works as follows. The software sweeps the current (bidirectional) through the magnet coils which produces a linear varying magnetic field. A waveform generator continuously drives an additional set of Helmholtz coils with a sinusoid which allows for field modulation. The received modulated current signal first is conditioned (current-to-voltage conversion, amplification, and filtering) and then sampled at a high rate through an analog-to-digital converter. This signal is then demodulated in software. Signal processing algorithms are utilized to precisely calculate the field of the observed response. A shift in the zero field response indicates that an external magnetic field is present as illustrated in FIG. 6. The magnetic field is easily measured by calculating the shift in the response from zero magnetic field, the ideal response. The measured field is the $B_{offset}$. In this schematic illustration, $B_{offset}$ is 15 Gauss. The measured field illustrated was chosen merely to make the underlying principle clear. However, much smaller local fields could and generally would be utilized in the measurement.

This sensor has many advantages over using a conventional Hall based sensor. Unlike Hall sensors, the measurement is completely independent of temperature and works especially well at lower fields ($\leq 0.1$ G or $\leq 10^{-2}$ mT). Also, this sensor is capable of indicating magnetic polarity. Therefore, this sensor can easily be applied in three dimensions which allows the technology to be used as a 3 dimensional magnetic field mapping sensor.

Miniature Zero- and Low-Field Spectrometer

Semiconductor companies evaluate performance and reliability of the solid-state devices they fabricate, generally utilizing characterization solely based upon electrical measurements. Electrical measurements provide absolutely no information about the physical and chemical nature of the performance limiting defects at the atomic level. Magnetic resonance measurements are capable of providing this information. If the manufacturer wanted to obtain this atomic scale information they could seek outside help from academic laboratories equipped for magnetic resonance. However, the possibility of the preferable approach of doing this work in house is discouraged by the aforementioned cost and complexity of the currently available apparatus as well as the difficulty of interpretation of the spectra that are acquired. Our sensor will allow these companies to perform their own research on the devices during and just after fabrication. This will save the company time and money. Our sensor will provide very straightforward measurements, though in some cases, at the cost of some loss in analytical power over the high-field and frequency EDMR spectrometers.

Figure 7:
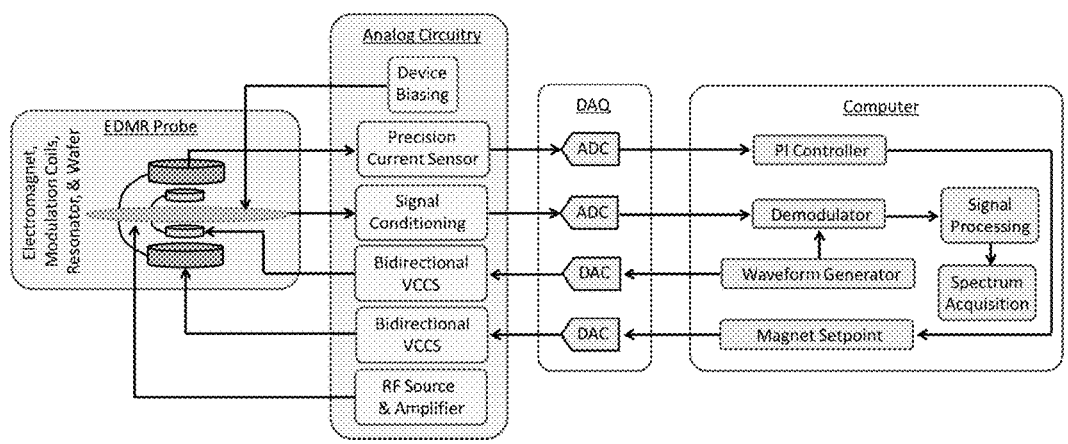
FIG. 7 is a diagram of a present preferred embodiment of a miniature spectrometer for wafer probing stations in accordance with the present invention.

The circuit previously described for the magnetic field sensor can also serve as a miniature EDMR spectrometer with the addition of circuitry to provide a relatively low-frequency (10-500 MHz) oscillating electromagnetic field as illustrated in FIG. 7.

Figure 8:
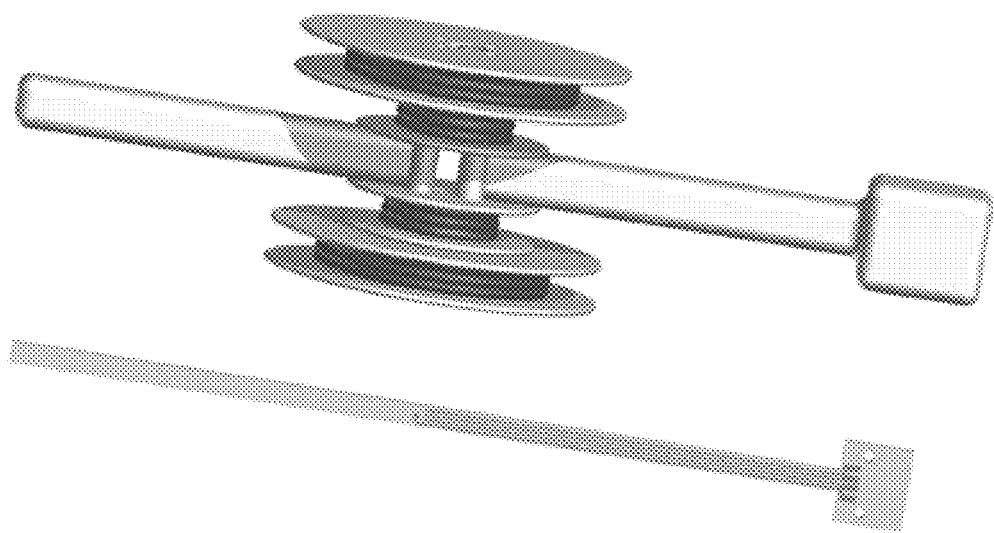
FIG. 8 is a perspective view of an electromagnet with (bottom) sample mount that can be utilized for the miniature spectrometer. A slight modification to the frame would allow it be used with wafer probing stations.

The powerful combination of low-field resonance spectroscopy and zero-field spin dependent transport spectroscopy would allow for the physical and chemical identification of atomic scale defects which limit the performance of solid-state devices. Because the technology is miniaturized, one could envision that it could serve as a standalone miniature spectrometer or easily be added to existing wafer probing stations. As a result, semiconductor manufacturing companies could study these important defects with spin dependent properties possibly during or just after fabrication of wafers and devices. The physical mechanism in which the data is gathered is identical to that of the magnetic field sensor. The only difference in the apparatuses is the addition of the circuitry used to generate the low-frequency oscillating electromagnetic field. FIG. 8 illustrates one realization of the electromagnet (for linear swept magnetic field) and device mount that could be used for the standalone spectrometer. A slight modification to this electromagnet would allow it to be used with wafer probing stations.

Figure 9:
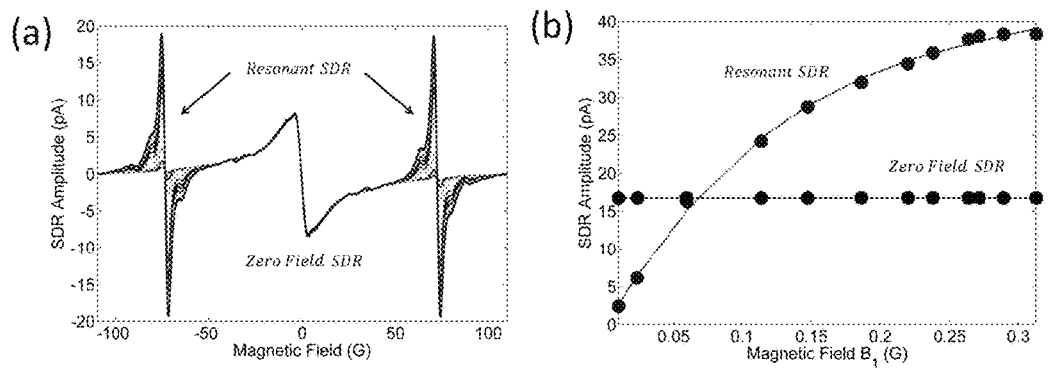
FIG. 9(a) is a graph of representative low-field EDMR traces for different oscillating field amplitudes.
FIG. 9(b) is a graph of amplitudes of the resonant and zero-field signals as a function of oscillating field amplitude which illustrates a representative EDMR spectrum acquired at low magnetic fields.

FIG. 9 illustrates representative spectra acquired at low magnetic fields of SDR in the base-collector junction of a 4H SiC BJT. As illustrated, this technology will allow for the data acquisition of resonant and zero-field spin dependent phenomenon in a wide variety of micro- or nano-electronic device. Representative low-field EDMR traces for different oscillating field amplitudes and amplitudes of the resonant and zero-field signals as a function of oscillating field amplitude are shown in FIGS. 9(a) and 9(b). This data set demonstrates that an oscillating magnetic field is not needed to observe an SDR response in a fully processed device; however, the utilization of it can provide additional information when combined with zero-field spectroscopy. All of the little "bumps" in the spectra are real. Their presence indicates electron-nuclear hyperfine interactions which are essentially unique for each type of performance limiting defect. An analysis of the SDR amplitude versus field will thus generally allow the identification of the physical and chemical nature of the observed defects.

Figure 10:
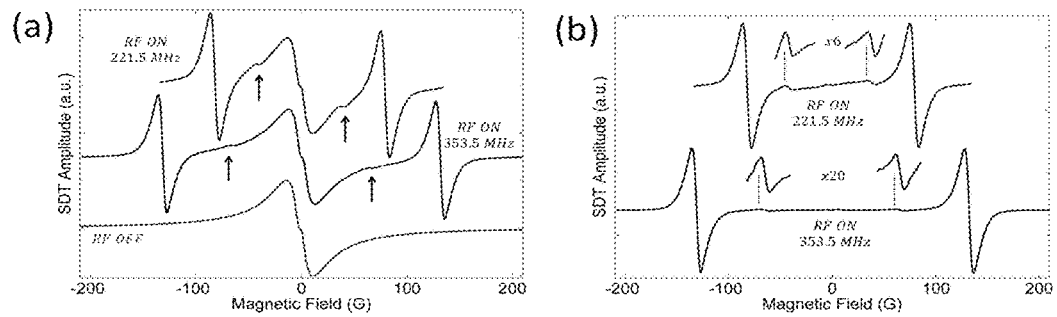
FIG. 10(a) is an illustration of spectra acquired with (v=221 MHz and v=353 MHz) and without the oscillating and magnetic field. (The arrows indicate the presence of the half-field signals.)
FIG. 10(b) is an illustration of both spectra acquired with application of oscillating magnetic field with the zero-field signal subtracted off.

In addition, for some measurements, the spectrometer will permit the detection of a half-field "forbidden" resonance signal. The ratio of integrated intensities of the half-field to full-field signals will allow for the extraction of a defect density. It is known that the measurement of magnetic resonance spectra at the standard resonance frequency and half that frequency can yield a defect density in conventional EPR. (This is discussed in standard textbooks such as the classic texts by C. P. Slichter.) The measurement has generally been impossible for solid state systems of interest because the half-field response is too weak to be detectable. However, the strength of the half field response scales with the reciprocal of the measurement frequency squared. Since some EDMR detection schemes yield a frequency independent sensitivity, they may be carried out at almost any arbitrarily low frequency, yielding an almost arbitrarily high sensitivity for the half field response. This makes defect density extraction well suited for our low-field spectrometer. FIG. 10 illustrates the SDT detection of these forbidden signals in an amorphous SiC dielectric based capacitor.

As can be seen in FIG. 10 low-field SDT data acquired in an amorphous SiC dielectric capacitor demonstrates the possibility of detecting the forbidden half-field transition at low magnetic fields. In FIG. 10(a) a spectra acquired with (ν=221 MHz and ν=353 MHz) and without the oscillating and magnetic field is shown. The arrows indicate the presence of the half-field signals. In FIG. 10(b) both spectra acquired with application of oscillating magnetic field with the zero-field signal subtracted off are shown. By subtracting off the zero-field signal, one can more easily integrate the intensity of the half-field signals which leads to a more accurate calculation of the defect density within the device under observation.

While we have shown and described certain present preferred embodiments of our sensing apparatus our invention is not limited thereto but may be variously embodied within the scope of the following claims.

We claim:

1. A sensing apparatus for detecting and determining the magnitude of a static magnetic field, the apparatus comprising;
    a first set of coils capable of producing a sweeping, quasi static, magnetic field when driven by a direct current;
    a second set of coils, for magnetic field modulation, positioned between the first set of coils capable of producing an oscillating magnetic field when driven by an oscillating current;
    a precision, bipolar current controller which drives current through the first set of coils to create a linearly sweeping magnetic field;
    a signal generator which drives an oscillating current through the second set of coils to create an oscillating magnetic field to modulate the field produced by the first set of coils;
    a voltage biased, semiconducting device with a known, low magnetic field magnetoresistance properties positioned in between both sets of coils and having a semiconducting device current;
    an analog front end which conditions the semiconducting device current before being sampled;
    an analog-to-digital converter which samples the conditioned semiconducting device current; and
    a signal processing unit capable of demodulating the conditioned sampled semiconducting device current and recording changes in this signal as a function of sweeping, quasi static magnetic field.

2. The sensing apparatus of claim 1 wherein the first set of coils are Helmholtz coils.

3. The sensing apparatus of claim 1, wherein the second set of coils are Helmholtz coils.

4. The sensing apparatus of claim 1, wherein the semiconducting device contains many defects to increase the magnetoresistance response at low magnetic fields.

5. The sensing apparatus of claim 1, wherein the analog front end biases the semiconducting device with a DC voltage and conditions the device current using current-to-voltage conversion, amplification, high pass and low pass/antialiasing filtering.

6. The sensing apparatus of claim 1, wherein the signal processing unit is a personal computer, microprocessor, or microcontroller.

7. The sensing apparatus of claim 1, wherein the signal processing unit self-calibrates itself with the already known parameters of the measured magnetoresistance response.

8. The sensing apparatus of claim 1, wherein the signal processing unit calculates the static magnetic field by measuring the shift in the measured magnetoresistance response of the semiconducting device away from zero magnetic field.

9. An apparatus for detecting and identifying atomic scale defects in fully processed devices, the apparatus comprising;
    a first set of coils capable of producing a sweeping, quasi static, magnetic field when driven by a direct current;
    a second set of coils, for magnetic field modulation, positioned between the first set of coils capable of producing an oscillating magnetic field when driven by an oscillating current, the second set of coils spaced far enough apart to enclose a voltage biased, semiconducting device with an unknown resonant and zero-field magnetoresistance response and through which a semiconducting device current passes;

a precision, bipolar current controller which drives current through the first set of coils to create a linearly sweeping magnetic field;

a signal generator which drives an oscillating current through the second set of coils to create an oscillating magnetic field to modulate the field produced by the first set of coils;

a radio frequency circuit with a resonant component which provides an oscillating electromagnetic field in a direction perpendicular to that of the static magnetic field produced by the first set of coils;

an analog front end which conditions the semiconducting device current before being sampled;

an analog-to-digital converter which samples the conditioned semiconducting device current; and a signal processing unit capable of demodulating the conditioned sampled semiconducting device current and recording changes in this signal as a function of sweeping, quasi static magnetic field.

10. The defect detection apparatus of claim 9, wherein the first set of coils are Helmholtz coils.

11. The defect detection apparatus of claim 9, wherein the second set of coils are Helmholtz coils.

12. The defect detection apparatus of claim 9, wherein the resonant component is a surface coil, a solenoid, or a micro strip resonator.

13. The defect detection apparatus of claim 9, wherein the device under observation exhibits spin dependent transport phenomenon such as recombination, tunneling, scattering, and or hopping.

14. The defect detection apparatus of claim 9, wherein the device under observation is a diode, capacitor, bipolar junction transistor, metal oxide semiconducting field effect transistor, solar cell, or a memresistor.

15. The defect detection apparatus of claim 9, wherein the analog front end biases the device with a DC or AC voltage and conditions the device current using current-to-voltage conversion, amplification, high pass and low pass/antialiasing filtering.

16. The defect detection apparatus of claim 9, wherein the signal processing device is a personal computer, microprocessor, or microcontroller.

17. The defect detection apparatus of claim 9, wherein the resonant and magnetoresistance spectrum provide information about the defect under observation.

18. The defect detection apparatus of claim 9, wherein the ratio of the integrated intensities of the half-field to full-field signals provide information about the defect density of the device under study.

* * * * *